(12) United States Patent
Horinouchi et al.

(10) Patent No.: US 9,761,412 B2
(45) Date of Patent: Sep. 12, 2017

(54) ION MILLING APPARATUS AND SAMPLE PROCESSING METHOD

(71) Applicant: Hitachi High-Technologies Corporation, Minato-ku, Tokyo (JP)

(72) Inventors: Kento Horinouchi, Tokyo (JP); Atsushi Kamino, Tokyo (JP); Toru Iwaya, Tokyo (JP); Hisayuki Takasu, Tokyo (JP)

(73) Assignee: Hitachi High-Technologies Corporation, Tokyo (JP)

(*) Notice: Subject to any disclaimer, the term of this patent is extended or adjusted under 35 U.S.C. 154(b) by 0 days.

(21) Appl. No.: 15/306,510

(22) PCT Filed: May 9, 2014

(86) PCT No.: PCT/JP2014/062471
§ 371 (c)(1),
(2) Date: Oct. 25, 2016

(87) PCT Pub. No.: WO2015/170400
PCT Pub. Date: Nov. 12, 2015

(65) Prior Publication Data
US 2017/0047198 A1 Feb. 16, 2017

(51) Int. Cl.
*H01J 37/305* (2006.01)
*H01J 37/30* (2006.01)
(Continued)

(52) U.S. Cl.
CPC ............ *H01J 37/305* (2013.01); *G01N 1/32* (2013.01); *H01J 37/09* (2013.01); *H01J 37/20* (2013.01);
(Continued)

(58) Field of Classification Search
USPC ... 250/492.1, 492.21, 492.22, 492.23, 492.3, 250/515.1, 526; 204/298.01, 298.11,
(Continued)

(56) References Cited

U.S. PATENT DOCUMENTS 7,435,971 B2* 10/2008 Vanderberg ............. H01J 27/08
250/423 R
2008/0067443 A1* 3/2008 Todoroki ............... G01N 1/286
250/492.21
(Continued)

FOREIGN PATENT DOCUMENTS

JP 5-18873 A 1/1993
JP 11-271192 A 10/1999
(Continued)

OTHER PUBLICATIONS

International Search Report (PCT/ISA/210) issued in PCT Application No. PCT/JP2014/062471 dated Jun. 24, 2014 with English-language translation (four (4) pages).
Japanese-language Written Opinion (PCT/ISA/237) issued in PCT Application No. PCT/JP2014/062471 dated Jun. 24, 2014 (four (4) pages).

*Primary Examiner* — Bernard Souw
(74) *Attorney, Agent, or Firm* — Crowell & Moring LLP

(57) ABSTRACT

Provided is a technology for suppressing a heat rise in a sample, the heat rise being generated due to ion beam irradiation at a low acceleration voltage. A blocking plate, which is different from a mask, is disposed in front of a sample. The blocking plate has an opening that overlaps a processing surface, and ion beams pass only through the opening of the blocking plate, and in the areas excluding the opening, the ion beams are blocked by the blocking plate, and the sample is not irradiated thereby. Furthermore, the heat rise in the sample is further suppressed by cooling the blocking plate.

14 Claims, 4 Drawing Sheets

(51) Int. Cl.
 *G01N 1/32* (2006.01)
 *H01J 37/20* (2006.01)
 *H01J 37/09* (2006.01)

(52) U.S. Cl.
 CPC ..... *H01J 37/3053* (2013.01); *H01J 2237/045* (2013.01); *H01J 2237/3151* (2013.01)

(58) Field of Classification Search
 USPC .................................................. 204/298.36
 See application file for complete search history.

(56) References Cited

U.S. PATENT DOCUMENTS

| | | | | |
|---|---|---|---|---|
| 2011/0266465 | A1* | 11/2011 | Shichi | H01J 27/26 250/492.3 |
| 2013/0220806 | A1* | 8/2013 | Iwaya | H01J 37/3005 204/298.32 |
| 2013/0245989 | A1* | 9/2013 | Kadowaki | H01J 37/261 702/150 |
| 2016/0189927 | A1* | 6/2016 | Satoh | H01J 37/3045 250/492.21 |

FOREIGN PATENT DOCUMENTS

| | | |
|---|---|---|
| JP | 2007-14996 A | 1/2007 |
| JP | 2007-57486 A | 3/2007 |
| JP | 2009-170117 A | 7/2009 |

\* cited by examiner

ION MILLING APPARATUS AND SAMPLE PROCESSING METHOD

TECHNICAL FIELD

The present invention relates to an ion milling apparatus and a sample processing method and, for example, to technology to prevent damage to a sample upon milling the sample by an ion beam.

BACKGROUND ART

Ion milling apparatuses are installed with a sample in a vacuum exhausted sample camber, irradiates the sample with an argon ion beam applied with a voltage of approximately 10 kV or less without focusing, sputters atoms from a sample surface utilizing physical sputtering phenomenon, and polishes the sample surface without applying stress thereto. The ion milling apparatuses are used when a sample for a scanning electron microscope (SEM) or a transmission electron microscopy (TEM) is produced.

For example PTL 1 discloses an ion milling apparatus including a blocking plate (mask) formed by a material having a low sputtering yield (material which is not abrased even when an ion beam hits the material). This blocking plate (mask) blocks a part of a sample excluding an exposed part from an ion beam while exposing the part of the sample from an end surface of the blocking plate by approximately 50 to 200 μm. That is, performing ion beam irradiation while the sample is partially exposed results in processing of the sample into a shape corresponding to the end surface of the blocking plate.

CITATION LIST

Patent Literature

PTL 1: JP 2007-14996 A

SUMMARY OF INVENTION

Technical Problem

An ion beam of an ion milling apparatus has an acceleration voltage of approximately 10 kV and an ion beam current of approximately 200 μA and thus a calorific value generated by ion beam irradiation is approximately 2 J/s.

When a sample easily affected by heat, for example a low-melting sample such as resin, is processed, as disclosed in PTL 1, a blocking plate (mask) and a sample stage are connected to a cooling source and the sample is thereby cooled. With a sample easily affected by heat (e.g. rubber, glass, etc.), however, cooling from a cooling source cannot result in an enough cooling effect as compared to an increase in calorific value of the sample by an ion beam.

In order to mitigate thermal damage to the sample by the ion beam, therefore, there is a method to irradiate with an ion beam at a low acceleration voltage of approximately 3 kV without changing magnetic force of the ion beam of a penning type in consideration to maintainability and operability and to thereby mitigate thermal damage to the sample.

With an unfocused ion beam, however, lowering the acceleration voltage results in an enlarged irradiation area of the sample with the ion beam and thus an area of the sample having a high temperature is also enlarged. Usually, a sample having low thermal conductivity receives more supply of heat by ion beam irradiation than heat transfer to a sample holder, a sample stage, and a blocking plate (mask). Therefore, the temperature of the sample rises higher than a melting point and as a result thermal damage cannot be prevented, thereby causing deformation of the sample.

The present invention has been devised in consideration to such circumstances. The present invention provides technology to mitigate thermal damage to a sample by ion beam irradiation at a low acceleration voltage.

Solution to Problem

In order to achieve the above object, in the present invention, in an ion milling apparatus, a beam irradiation area limiting member to limit an irradiation area of a sample with an ion beam is disposed between a sample mask and an ion source. This beam irradiation area limiting member limits the irradiation area with the ion beam spread at a low acceleration voltage of approximately 3 kV, thereby avoiding a part of the sample excluding an observation processing part from being irradiated with the ion beam. This allows for mitigating thermal damage to the sample.

Further characteristics related to the present invention will be made clear from the descriptions herein and the accompanying drawings. Moreover, an embodiment of the present invention is achieved and implemented by a combination of an element and various elements and the following detailed descriptions and accompanying aspects of the present invention.

Advantageous Effects of Invention

The present invention allows for suppressing thermal damage to a sample.

DESCRIPTION OF EMBODIMENTS

Hereinafter, embodiments of the present invention will be described with reference to the accompanying drawings. In the accompanying drawings, components having the same function may be denoted by the same numerical symbol. Incidentally, the accompanying drawings illustrate specific embodiments and exemplary implementation according to the principal of the present invention; however, these drawings are for the purpose of understanding of the present invention and thus are never used for limited interpretation of the present invention.

In the present embodiment, descriptions are made in a sufficiently detailed manner for a person skilled in the art to implement the present invention. However, other implementation or another embodiment is also possible. It is necessary to understand that a configuration or a structure may be changed or various elements may by replaced without departing from the scope and spirits of the technical idea of the present invention. Therefore, the following descriptions shall not be interpreted in a limiting manner.

An embodiment of the present invention relates to an ion milling apparatus to irradiate, with an ion beam, an observation/analysis surface of a sample to be observed by a scanning electron microscope (SEM), a transmission electron microscopy (TEM), or the like and to form a target observation surface. Especially, the embodiment relates to an ion milling apparatus to form an observation surface of a sample easily affected by heat. The embodiment is described with an example of an ion milling apparatus mounted with an ion source to irradiate with an argon ion beam; however, the ion beam is not limited to argon ion beams and various ion beams may be employed.

<Configuration of Ion Milling Apparatus>

Figure 1:
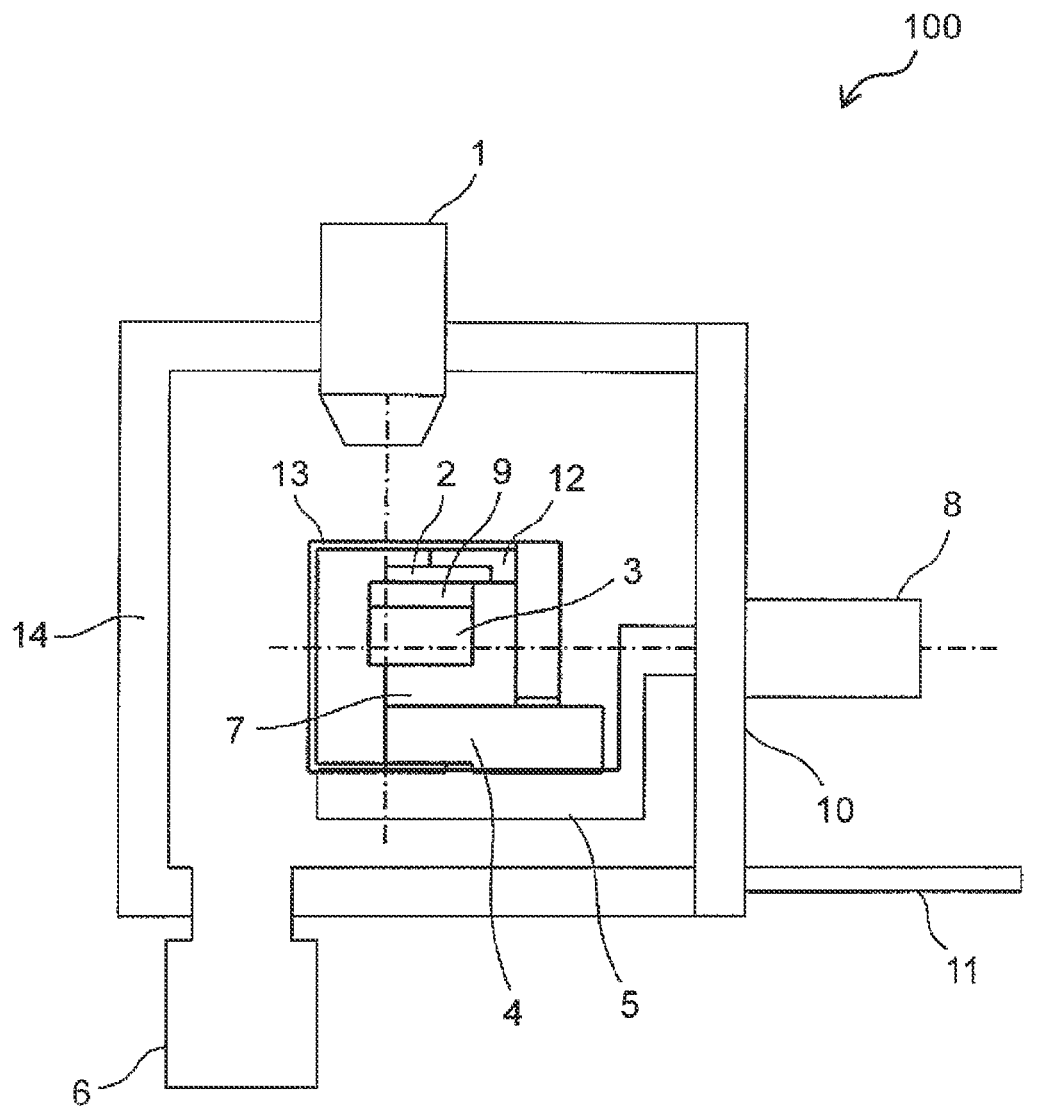
FIG. 1 is a diagram illustrating a schematic configuration of an ion milling apparatus according to an embodiment of the present invention.

FIG. 1 is a diagram illustrating a configuration of an ion milling apparatus according to an embodiment of the present invention. The ion milling apparatus 100 includes a vacuum chamber 14, a vacuum exhausting system 6, a linear guide 11, an ion source 1 installed on a top surface of the vacuum chamber 14, and a sample stage 8 installed on a front surface of the vacuum chamber 14.

The vacuum chamber 14 is provided with a sample unit base 5. The sample unit base 5 is mounted with a sample mask unit micromotion mechanism 4. As for a mounting method, a lower surface of the sample mask unit micromotion mechanism 4 (surface side opposite to a mask surface irradiated with an ion beam) and a top surface of the sample unit base 5 are brought into contact and fixed to each other with a screw. The sample unit base 5 is configured to allow rotational inclination at an arbitrary angle relative to an optical axis of an ion beam. A direction and an inclination angle of rotational inclination are controlled by the sample stage 8. Allowing the sample stage 8 to rotationally incline al lows for setting a sample holder 7 and a sample 3, installed on the sample mask unit micromotion mechanism 4, at a predetermined angle relative to the optical axis of the ion beam. Furthermore, a rotational inclination axis of the sample stage 8 and a position of a top surface of the sample (lower surface of the mask) are allowed to correspond with each other, thereby efficiently producing a smooth processing surface.

The sample unit base 5 is disposed via the sample stage 8 (rotation mechanism) mounted to a flange 10 that is also a part of container wall of the vacuum chamber 14. When the flange 10 is pulled out along the linear guide 11 to release the vacuum chamber 14 to the atmospheric state, the sample unit base 5 is pulled out from the vacuum chamber 14. In this manner, a sample stage pull-out mechanism is configured.

The sample unit base 5 is further configured to allow rotational inclination at an arbitrary angle relative to the optical axis of the ion beam. A direction and an inclination angle of rotational inclination are controlled by the sample stage 8. Therefore, allowing the sample stage 8 to rotationally incline allows for setting the sample 3, installed on the sample holder 7, at a predetermined angle relative to the optical axis of the ion beam. Furthermore, a rotational inclination axis of the sample stage 8 and a position of a top surface of the sample (lower surface of the mask) are allowed to correspond with each other, thereby efficiently producing a smooth processing surface.

The sample mask unit micromotion mechanism 4 is configured to allow movement along longitudinal and transversal directions vertical to the optical axis of the ion beam, that is, in an X direction and a Y direction. The sample holder 7 is thus also configured to allow movement along the longitudinal and transversal directions vertical to the optical axis of the ion beam, that is, in the X direction and the Y direction.

A sample holding member 9 further firmly foxes the sample 3 and is formed by resin or the like for example. The sample holding member 9 is abrased together with the sample 3 and is replaced every time the sample 3 is subjected to milling.

A mask (blocking plate) 2 is disposed while in contact with the sample holding member 9 or the sample to allow only an end portion of the sample 3 to be exposed and to allow only the exposed part to be subjected to milling by the ion beam. The mask (blocking plate) 2 is fixed by a mask holder 12. Incidentally, the mask 2 and the mask holder 12 may be formed integrally. In this case, however, the mask 2 is often abrased by preceding milling operation and thus it is desirable to replace the mask and the mask holder of an integrated type at each milling operation.

Furthermore, a slit-including blocking plate 13 is disposed in such a manner as to cover the mask 2. The ion beam emitted from the ion source 1 is limited of its irradiation area by the slit-including blocking plate 13, thereby avoiding the sample 3 from irradiated with the ion beam corresponding to an area exceeding the width of the slit. The slit-including blocking plate 13 includes a folded part 131 extending downward from an end thereof by a predetermined length. This folded part 131 prevents the sample from being irradiated with the ion beam escaped.

Furthermore, cooling the slit-including blocking plate 13 by bringing the folded part 131 of the slit-including blocking plate 13 into contact with the sample mask unit micromotion mechanism 4 also cools the sample mask unit micromotion mechanism 4, thereby allowing for improving heat radiating effect of the sample 3.

The sample mask unit micromotion mechanism 4 has a micromotion structure with one axis or two axes independent from a sample planar moving means with two axes. Moreover, the sample, the blocking plate, and each of the micromotion structures are easily attachable to and detachable from the ion milling main body. An ion beam irradiation position and a position of the sample can be ad lusted under observation by an optical microscope.

<Problems of General Ion Milling Apparatus>

In the ion milling apparatus 100 for producing a sample for electron microscopes, irradiation conditions of an ion beam are for example an acceleration voltage of approximately 10 kV or less and an ion beam current of approximately 200 µA or less. A calorific value given to the sample by ion beam irradiation can be calculated as Joule heat where the acceleration voltage is multiplied by the ion beam current. With the above acceleration voltage and the ion beam current, the calorific value is approximately 2 J/s or less.

In the ion milling apparatus 100, in order to obtain a sample surface required for analysis or observation, ion beam irradiation of the sample may require to be performed for several hours. Here, with a low-melting sample such as resin, deformation or damage due to a temperature rise of the sample by ion beam irradiation cannot be ignored.

In order to suppress a temperature rise of the sample by ion beam irradiation, it is possible to use a sample holding means capable of effectively transferring heat by ion beam irradiation from the sample to a sample holding structure or the like or to use a means to reduce ion beam irradiation thermal energy and to thereby suppress a temperature rise of the sample. By using a means to suppress a temperature rise of the sample 3, reducing an acceleration voltage can suppress the calorific value generated by ion beam irradiation. Under conditions of an acceleration voltage of approximately 3 kV and an ion beam current of approximately 200 μA or less, a calorific value given to the sample by ion beam irradiation is approximately 0.6 J/s. This is approximately one third as compared to a calorific value with an ion beam with an acceleration voltage of approximately 10 kV.

However, the ion beam of the penning type of the ion milling apparatus 100 does not focus the ion beam and thus, when the acceleration voltage is approximately 3 kV, the ion beam spreads and an ion beam irradiation area of the sample increases as compared to that at an acceleration voltage of approximately 10 kV.

As a result, the effect of suppressing the temperature rise of the sample by ion beam irradiation with low acceleration becomes small.

In the embodiment of the present invention, therefore, as described above, the ion milling apparatus 100 includes a mechanism mounted with the new slit-including blocking plate 13.

<Configuration of Slit-Including Blocking Plate>

Figure 2:
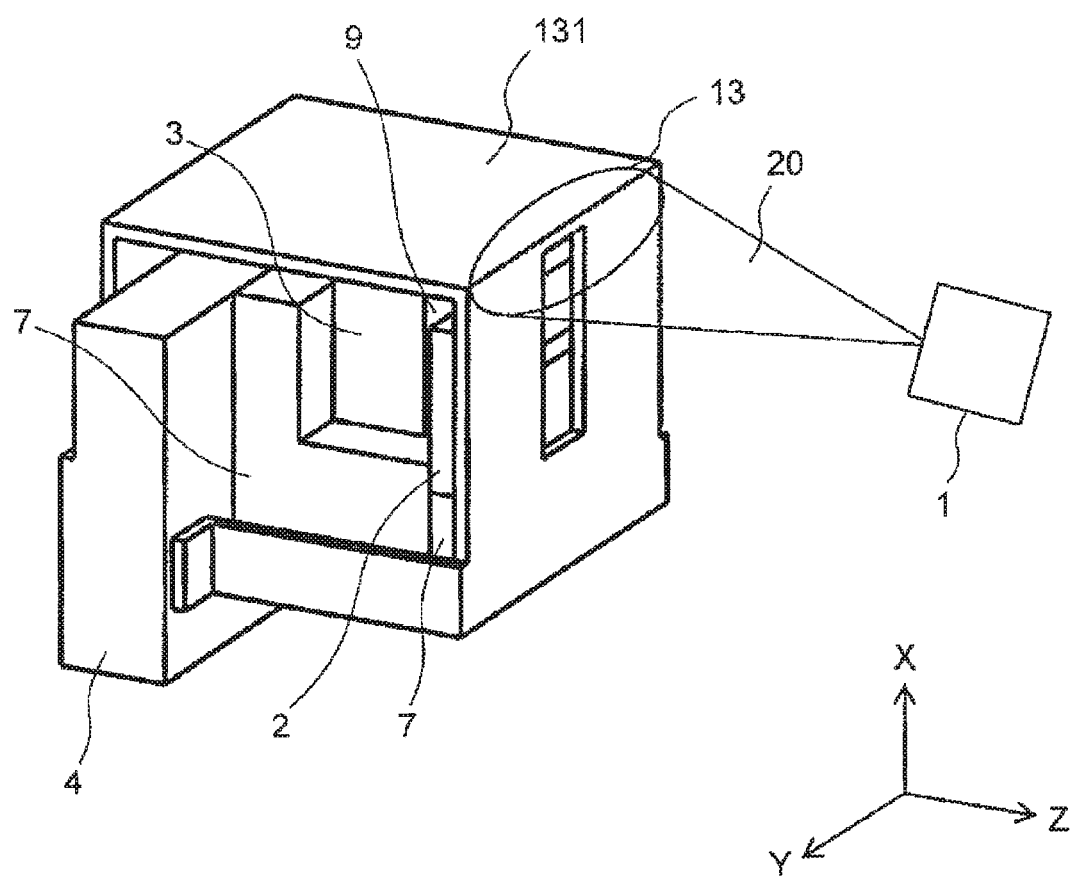
FIG. 2 is a diagram illustrating a structure near a sample stage of the ion milling apparatus.

FIG. 2 is a diagram illustrating a configuration of each member mounted to the sample unit base 5. Especially in the present embodiment, the slit-including blocking plate 13 is provided anew in order to solve the above problem. Specifically, the slit-including blocking plate 13 including an opening (slit) in the central part of the blocking plate is installed in front of the sample and the mask 2 (front side on the paper surface). The slit-including blocking plate 13 is installed and fixed such that the opening thereof overlaps with an observation surface of the sample 3.

With the above mechanism, an ion beam 20 at a low acceleration voltage of approximately 3 kV is emitted toward the slit-including blocking plate 13, the mask (blocking plate) 2, and the sample 3. The slit-including blocking plate 13 is first irradiated with the ion beam spread with the low acceleration voltage. A part of the slit-including blocking plate 13 excluding the opening (slit) is blocked of the ion beam 20 and thus only the ion beam 20 that is emitted at the opening passes through the slit-including blocking plate 13.

The mask (blocking plate) 2 and the sample 3 (and the sample holding member 9) are irradiated with the ion beam 20 having passed through the slit-including blocking plate 13. Since only an observation processing surface is irradiated, in a state where thermal damage to the sample 3 is mitigated, it is possible to process the sample into a shape corresponding to the end surface of the mask (blocking plate) 2.

The shape of the opening of the slit-including blocking plate 13 may be any shape as long as other part than the observation surface can be blocked thereby. Here, the opening is a slit but may have a round shape or an elliptical shape. Therefore, the slit-including blocking plate 13 can be simply referred to as a beam irradiation area limiting member (means) to limit an irradiation area of the ion beam 20.

The slit-including blocking plate 13 includes a folded part 131 extending vertically toward the sample holder 7 from an end portion thereof. This folded part 131 allows for preventing the ion beam 20 from escaping and thereby avoiding irradiation, with the ion beam 20, of other unnecessary part of the sample 3.

Incidentally, the slit-including blocking plate 13 is mounted to the sample unit base 5 as illustrated in FIG. 1. Note that as will be described later in a variation, the slit-including blocking plate 13 may be mounted in front of the sample unit base 5 as a separate unit. When mounted to the sample unit base 5, the slit-including blocking plate 13 is not interlocked with a mask fine adjustment mechanism (not illustrated) to adjust a position of the sample 3 and to thereby determine a part of the sample 3 exposed from the mask 2 but is installed in such a manner as to cover the mask (blocking plate) 2 and the sample 3 by the slit-including blocking plate 13 and fixed with a screw. By covering the mask (blocking plate) 2 and the sample 3 by the slit-including blocking plate 13 thereover, the slit-including blocking plate 13 can function as a fixing member of the mask (blocking plate) 2 and the sample 3.

Moreover, the slit-including blocking plate 13 is not required to be formed by a material with a low sputtering yield. In the ion milling apparatus 100 including a cooling mechanism, therefore, by forming the slit-including blocking plate 13 by a material (e.g. copper) having thermal conductivity higher than that of the mask 2 and cooling the slit-including blocking plate 13, heat radiating effect of the mask (blocking plate) 2 or the sample 3 may be improved and the effect of suppressing thermal damage to the sample 3 by the ion beam 20 may be further enhanced.

Furthermore, by bringing the folded part 131 of the slit-including blocking plate 13 into contact with the sample mask unit micromotion mechanism 4, the sample mask unit micromotion mechanism 4 can be cooled via the slit-including blocking plate 13, thereby allowing for improving heat radiating effect of the sample 3.

The above configuration allows for suppressing heat damage to the sample by ion beam irradiation at a low acceleration voltage in the ion milling apparatus.

<Variation>

Figure 3:
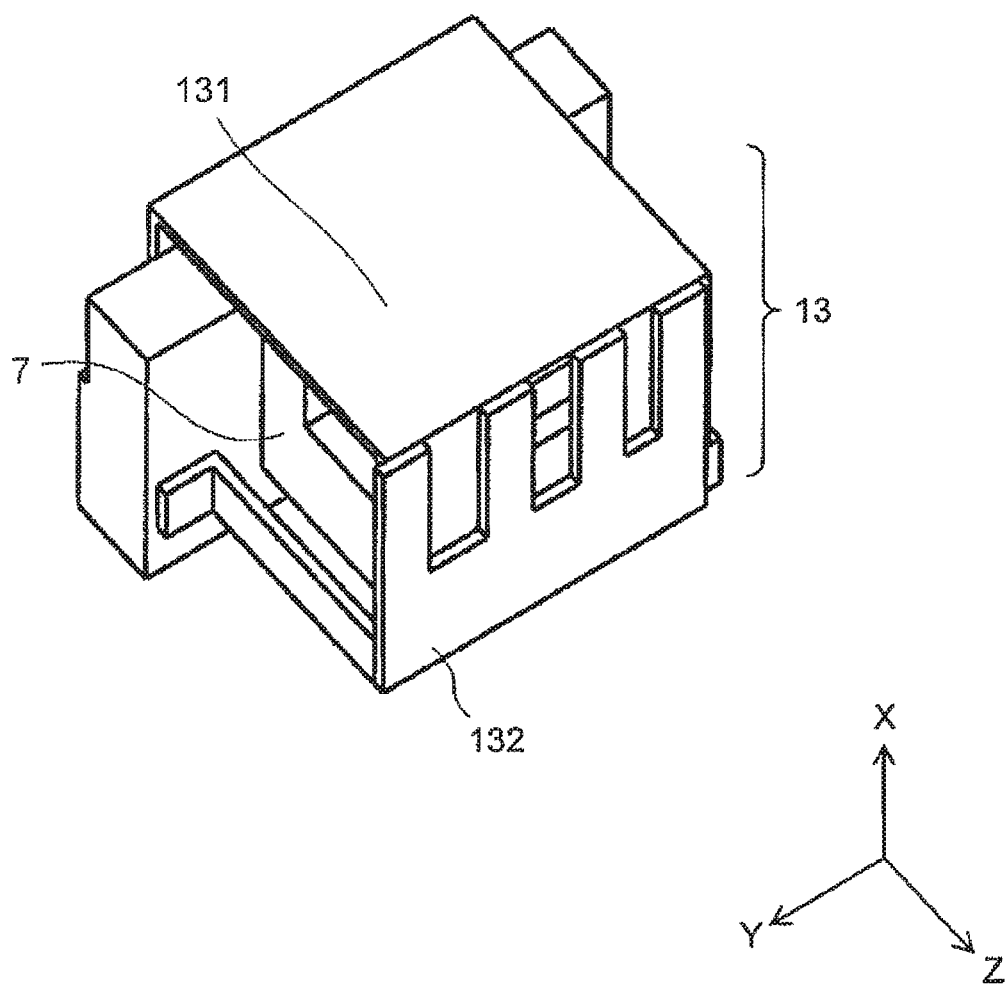
FIG. 3 is a diagram illustrating another configuration (variation) of a slit-including blocking plate.

(1) FIG. 3 is a diagram illustrating another exemplary configuration of the slit-including blocking plate 13. The slit-including blocking plate 13 includes a slit plate 132 including slits having widths of a plurality of kinds, and a folded part 131 extending from an end portion of the slit plate 132 toward a sample holder.

The slit plate 132 includes the slits having the plurality of different widths. This slit plate 132 slides in the Y direction by a slit plate moving mechanism (not illustrated). This allows for executing milling processing by changing to a desired slit width. The slit plate 132 may be attachable and detachable. In this case, a plurality of kinds of slit plates including slits having a plurality of different widths may be prepared to allow for replacement to a slit plate desired by a user. Meanwhile, the folded part 131 is fixed to a sample holder 7. Incidentally, the slit plate 132 may include a fixed slit plate and a movable slit plate and a desired slit width may be implemented by moving the movable slit plate in the Y direction.

Figure 4:
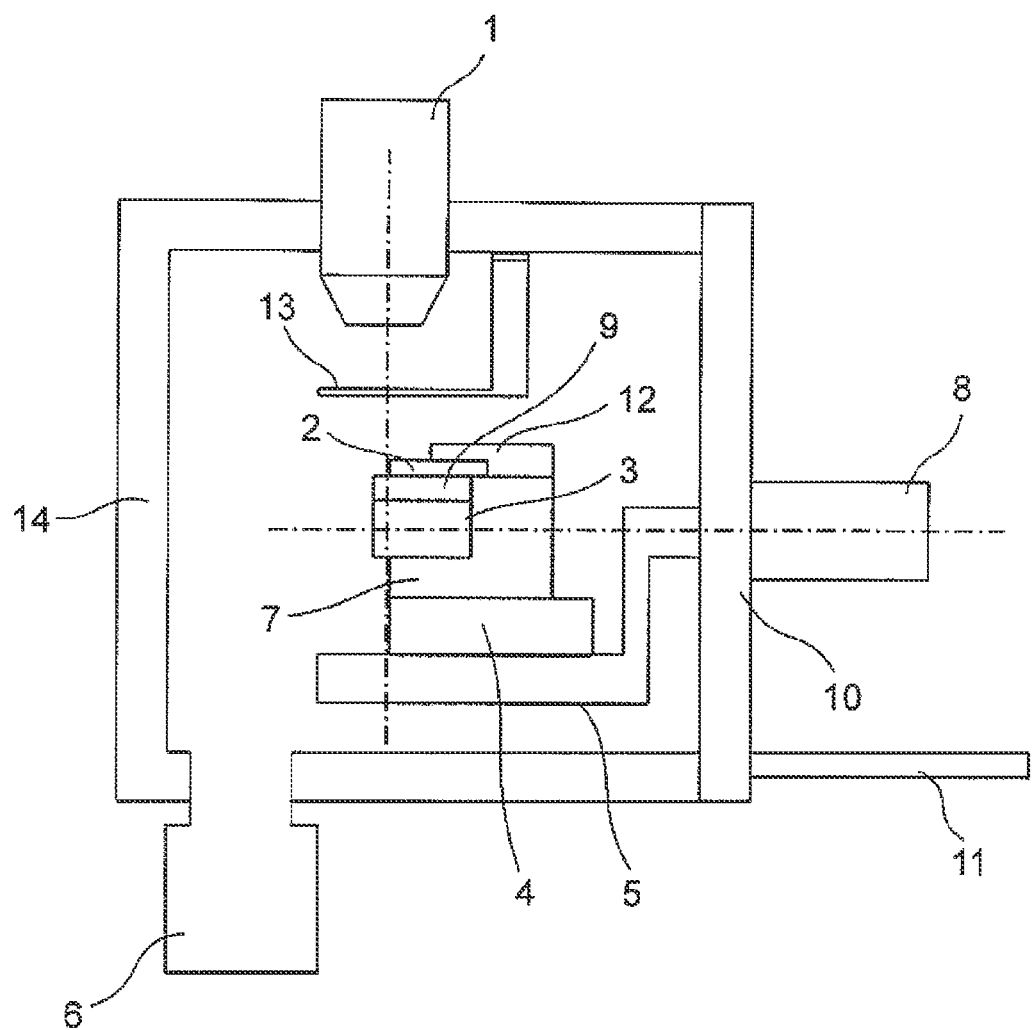
FIG. 4 is a diagram illustrating a configuration of a variation of the ion milling apparatus.

(2) FIG. 4 is a diagram illustrating a configuration of a variation of the ion milling apparatus 100. In this variation, a slit-including blocking plate 13 is not in contact with the mask 2 or the sample 3 but is installed above the mask 2 and the sample 3 (in a space between an ion source 1 and a mask 2). As for attachment, for example, an end part of the slit-including blocking plate 13 may be fixed to a ceiling plane of the vacuum chamber 14 such that the slit-including blocking plate 13 extends therefrom. Incidentally, in this case, the folded part 131 as descried in the aforementioned embodiments may not be provided. This is because escaping of the ion beam 20 is not required to be considered.

<Summary>

In the ion milling apparatus according to the embodiment of the present invention, when an acceleration voltage of an ion beam is set at approximately 3 kV, the ion beam spreads and thus a limiting member to limit the spread irradiation area is provided between the mask and the ion source. The limiting member is implemented by the blocking plate including a slit having a predetermined width, an opening of a predetermined size, or the like. Providing the limiting member in the above manner allows for reducing an area of the sample irradiated with the ion beam. Therefore, disadvantage that a sample easily affected by heat is deformed by the heat of the ion beam can be avoided.

An appropriate combination of the plurality of components disclosed in the embodiments can form various aspects of the invention. Moreover, some components may be omitted from among all the components described in the embodiment. Furthermore, components of different embodiments may be incorporated as appropriate. The present invention has been described relating to a specific example; however, it should be noted that in every respect these descriptions are made for the purpose of explaining but for limiting. The present description and the specific examples are those that are merely typical. The scope and the spirit of the present invention are presented by the claims that follow.

REFERENCE SIGNS LIST 1 ion source
2 mask (blocking plate)
3 sample
4 sample mask unit micromotion mechanism
5 sample unit base
6 vacuum exhausting system
7 sample holder
8 sample stage
9 sample holding member
10 flange
11 linear guide
12 mask holder
13 slit-including blocking plate
14 vacuum chamber
20 ion beam

The invention claimed is:
1. An ion milling apparatus to irradiate a sample with an ion beam and to thereby perform milling of the sample, the ion milling apparatus comprising:
 an ion source to emit the ion beam;
 a sample holder to fix the sample by placing the sample thereon;
 a sample mask to cover the sample and to allow only a part of the sample to be exposed as a target of milling; and
 a beam irradiation area limiting member, disposed between the sample mask and the ion source, to limit an irradiation area of the sample with the ion beam.
2. The ion milling apparatus according to claim 1, further comprising:
 a mask holder to fix the sample mask,
 wherein the beam irradiation area limiting member is installed in contact with the mask holder.
3. The ion milling apparatus according to claim 2,
 wherein the beam irradiation area limiting member comprises a folded part, extending from an end portion of the beam irradiation limiting member, to prevent the ion beam from escaping.
4. The ion milling apparatus according to claim 1,
 wherein the beam irradiation area limiting member is disposed spatially apart from the sample mask.
5. The ion milling apparatus according to claim 1,
 wherein the beam irradiation area limiting member is a blocking plate including a slit having a predetermined width or an opening of a predetermined size.
6. The ion milling apparatus according to claim 1,
 wherein the beam irradiation area limiting member is configured by a blocking plate including slits having a plurality of different widths, and
 the ion milling apparatus further comprises a blocking plate moving mechanism to move the beam irradiation area limiting member and to thereby allow each of the slits having the plurality of different widths to be opposite to an exposed part of the sample.
7. The ion milling apparatus according to claim 2, further comprising:
 a cooling mechanism to cool the beam irradiation area limiting member.
8. The ion milling apparatus according to claim 7,
 wherein the beam irradiation area limiting member is formed by a material having thermal conductivity higher than that of the sample mask.
9. A sample processing method to irradiate a sample with an ion beam and to process the sample by performing ion milling of the sample, the method comprising the steps of:
 placing the sample on a sample holder;
 placing, on the sample placed on the sample holder, a sample mask to cover the sample and to allow only a part of the sample to be exposed as a target of milling;
 disposing, between the sample mask and the ion source, a beam irradiation area limiting member to limit an irradiation area of the sample with the ion beam; and
 allowing an exposed part of the sample to be irradiated with an ion beam emitted from the ion source at an acceleration voltage of approximately 3 kV via the beam irradiation area limiting member.
10. The sample processing method according to claim 9,
 wherein the beam irradiation area limiting member is installed in contact with a mask holder to fix the sample mask.
11. The sample processing method according to claim 10,
 wherein the beam irradiation area limiting member comprises a folded part, extending from an end portion of the beam irradiation limiting member, to prevent the ion beam from escaping.
12. The sample processing method according to claim 9,
 wherein the beam irradiation area limiting member is disposed spatially apart from the sample mask.
13. The sample processing method according to claim 9,
 wherein the beam irradiation area limiting member is a blocking plate including a slit having a predetermined width or an opening of a predetermined size.
14. The sample processing method according to claim 9,
 wherein the beam irradiation area limiting member is configured by a blocking plate including slits having a plurality of different widths, and
 a blocking plate moving mechanism moves the beam irradiation area limiting member and thereby allows each of the slits having the plurality of different widths to be opposite to an exposed part of the sample.

* * * * *